United States Patent
Guo et al.

(10) Patent No.: US 9,650,625 B1
(45) Date of Patent: May 16, 2017

(54) THERMOSTABLE PECTINASE

(71) Applicant: DONGGUAN APAC BIOTECHNOLOGY CO., LTD., Dongguan (CN)

(72) Inventors: Rey-Ting Guo, Taipei (TW); Ya-Shan Cheng, Taipei (TW); Jian-Wen Huang, Taipei (TW); Tzu-Hui Wu, Taipei (TW); Hui-Lin Lai, Taipei (TW); Cheng-Yen Lin, Taipei (TW); Tsung-Yu Ko, Taipei (TW)

(73) Assignee: DONGGUAN APAC BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 15/334,827

(22) Filed: Oct. 26, 2016

(30) Foreign Application Priority Data

Nov. 2, 2015 (TW) .............................. 104135987 A (51) Int. Cl.
*C12N 9/88* (2006.01)

(52) U.S. Cl.
CPC ........ *C12N 9/88* (2013.01); *C12Y 402/02002* (2013.01)

(58) Field of Classification Search
CPC .......................... C12N 9/88; C12Y 402/02002
See application file for complete search history.

(56) References Cited

U.S. PATENT DOCUMENTS

2010/0233780 A1* 9/2010 Aehle .................... C11D 3/386
435/189

* cited by examiner

*Primary Examiner* — Kagnew H Gebreyesus
(74) *Attorney, Agent, or Firm* — Kirton McConkie; Evan R. Witt (57) ABSTRACT

A pectinase having improved thermostability is disclosed. The pectinase has a modified amino acid sequence of SEQ ID NO: 2, wherein the modification is a substitution of serine at position 181 with phenylalanine, methionine or leucine.

6 Claims, 7 Drawing Sheets

| Mutant | Primer sequence |
|---|---|
| S181F | 5' - CCTTCTTTGACCGCC<u>TTC</u>GAGTCTACTGGTATC -3 ' (SEQ ID NO: 9) |
| S181M | 5' - CCTTCTTTGACCGCC<u>ATG</u>GAGTCTACTGGTATC -3 ' (SEQ ID NO: 10) |
| S181L | 5' - CCTTCTTTGACCGCC<u>TTG</u>GAGTCTACTGGTATC -3 ' (SEQ ID NO: 11) |

FIG. 3

FIG. 4
- SEQ ID NO: 3
- SEQ ID NO: 4

```
gatggtgacggtacaacagcctctatcgagcaaatcttgagaaaccagagacctgacggtggatggagaaaggactattctgtcacctct
 D  G  D  G  T  T  A  S  I  E  Q  I  L  R  N  Q  R  P  D  G  W  R  D  Y  S  V  T  S ggagaatgggcaaagtctaccattgacaacaaagcaacatacaccgagatcagaagattggccgcagaatacaccaagacaagagattct
 G  E  N  G  K  S  T  I  D  N  K  A  T  Y  T  E  I  R  K  L  A  A  E  Y  T  K  T  R  S agatattctgacgccgcgtcagaggaatccacttcttgttgaacatgcaatacgcaaacggtggttgcctcagatctatcagggaact
 R  Y  S  D  A  A  V  R  G  I  N  F  L  L  N  M  Q  Y  A  N  G  G  F  Q  I  Y  Q  G  T ggttaccacagacatatcacctacaacgacaacgctatgatcaacgtcatgttgttggatgatgtcgccaacagaagaggagatttt
 G  Y  H  R  I  I  T  Y  N  D  N  A  M  I  N  V  M  L  L  D  D  V  A  N  R  R  G  D  F gccttcgttaacacatctttggccgatcagtctagagccgcgttactagaggtgttgattgcatttgagaacacaggttgtcgccggt
 A  F  V  N  T  S  L  A  D  Q  S  R  A  A  V  T  R  G  V  D  C  I  L  R  T  Q  V  V  A  S ggaagattgactgcttggggtcagcaaaatgactccgtctattggccaccagcaggagctagatcttacgaagtccattcttgaccgcc
 G  R  L  T  A  W  G  Q  Q  N  D  S  V  S  L  A  P  A  G  A  R  S  Y  E  V  P  S  L  T  A atgagtctactggtatcgtcagattctgaagaccagacacagacctctcagattagagcatctatccaggcagctgaagctggttc
 M  S  T  G  I  V  R  F  L  K  T  S  P  Q  T  S  Q  I  S  A  S  I  Q  A  A  K  A  N  F cagacgtcaaaatcaactggaatcagagtcgttaagacaacgacgatgttatcgtcgtcgaagatccatctgtcacaaccctatctgg
 Q  T  V  K  I  T  G  I  R  V  V  K  T  N  D  D  Y  I  V  V  E  D  P  S  V  T  T  F  I gccagattttacgaaatcggaaccaacagaccaatcttcgtcggtagagacggaatcgtcaagtacagattgtctgagatcgagcaggaa
 A  R  F  Y  E  I  G  T  N  R  P  I  F  V  G  R  D  G  I  V  K  Y  R  L  S  E  I  E  Q  E agaagaaccggttactcttggtacggtaattggccagcatcttgttt  - SEQ ID NO: 5
 R  R  T  G  Y  S  W  Y  G  N  W  P  A  S  L  F   - SEQ ID NO: 6
```

THERMOSTABLE PECTINASE

FIELD OF THE INVENTION

The present invention relates to a pectinase, and more particularly to a thermostable pectinase.

BACKGROUND OF THE INVENTION

Pectin, which is mostly found in the primary cell wall and in the middle lamella, is one of the main components of the plant cell wall. Pectic substances are complex heteropolysaccharides that are mainly composed of many D-galacturonic acid residues linked by α-1,4-bonds as a backbone of pectin. The backbone can be modified by methyl-esterification or substitution with acetyl groups. Pectins can be generally classified into three groups: homogalacturonan, xylogalacturonan and rhamnogalacturonan. The last one has the most complex structure that consists of repeating rhamnose-galacturonic acid residues branched with sugars like galactose, xylose and arabinose.

Because of the complicated architecture of pectin, its complete degradation requires several different pectinolytic enzymes, also known as pectinases, to work together. These enzymes are widely produced by bacteria, yeast, fungi and plants and basically include three types: hydrolases, lyases and esterases. Among these pectinolytic enzymes, pectate lyase (also named endopolygalacturonate lyase; EC 4.2.2.2) is one of the key enzymes for depolymerization of pectin. It can randomly catalyze the α-1,4-glycosidic bond on polygalacturonic acid via transelimination mechanism and generate unsaturated oligogalacturonate products.

Pectinases have been widely used in the food and wine industries for a long time. In addition, these enzymes are extensively applied in the papermaking process, textile industry and feed manufacture. Because the industrial pectinases have high economic value in industrial applications, many studies try to find better pectinases for industrial use by either searching new genes or modifying current enzyme. Protein engineering by rational design based on structural analysis is one of the major strategies for improvement of industrial enzyme. High thermostability is one of the ideal conditions for being a good industrial enzyme. A thermostable enzyme basically has higher protein stability and better performance of enzymatic hydrolysis that means the more benefits in business.

In the present invention, the crystal structure of a pectate lyase is analyzed and the thermostability of the pectate lyase is improved by rational design.

SUMMARY OF THE INVENTION

An object of the present invention is to modify a current pectate lyase by means of structural analysis and site-directed mutagenesis to efficiently improve its thermostability, and further increase its economic value of industrial application.

According to an aspect of the present invention, there is provided a pectinase comprising a modified amino acid sequence of SEQ ID NO: 2, wherein the modification is a substitution of serine at position 181 with phenylalanine, methionine or leucine.

In an embodiment, the amino acid sequence of SEQ ID NO: 2 is encoded by PcPEL gene isolated from *Paenibacillus campinasensis* BL-11.

In an embodiment, the pectinase is a pectate lyase.

In an embodiment, the pectinase has a full length amino acid sequence of SEQ ID NO: 4.

In an embodiment, the pectinase has a full length amino acid sequence of SEQ ID NO: 6.

In an embodiment, the pectinase has a full length amino acid sequence of SEQ ID NO: 8.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, the gene of the pectate lyase (PcPEL) was isolated from alkalophilic bacterium *Paenibacillus campinasensis* BL-11 strain, and the encoded enzyme showed its optimal activity at 50° C., pH 10 according to a previous study. To improve the thermostability of this pectate lyase, the enzyme was modified by site-directed mutagenesis based on its structural information. For understanding the structural information and the catalytic mechanism of this enzyme, the protein structure of PcPEL was solved by X-ray crystallography. According to the structural analysis, serine at position 181 where is near the active site of the enzyme was chosen and mutated to phenylalanine, methionine and leucine, respectively, by site-directed mutagenesis. As a result, the present invention successfully improves the thermostability of PcPEL and further enhances the economic value of this pectate lyase for industrial application. The enzyme modification process of PcPEL and the resulted protein are described in detail as follows.

Figure 1:
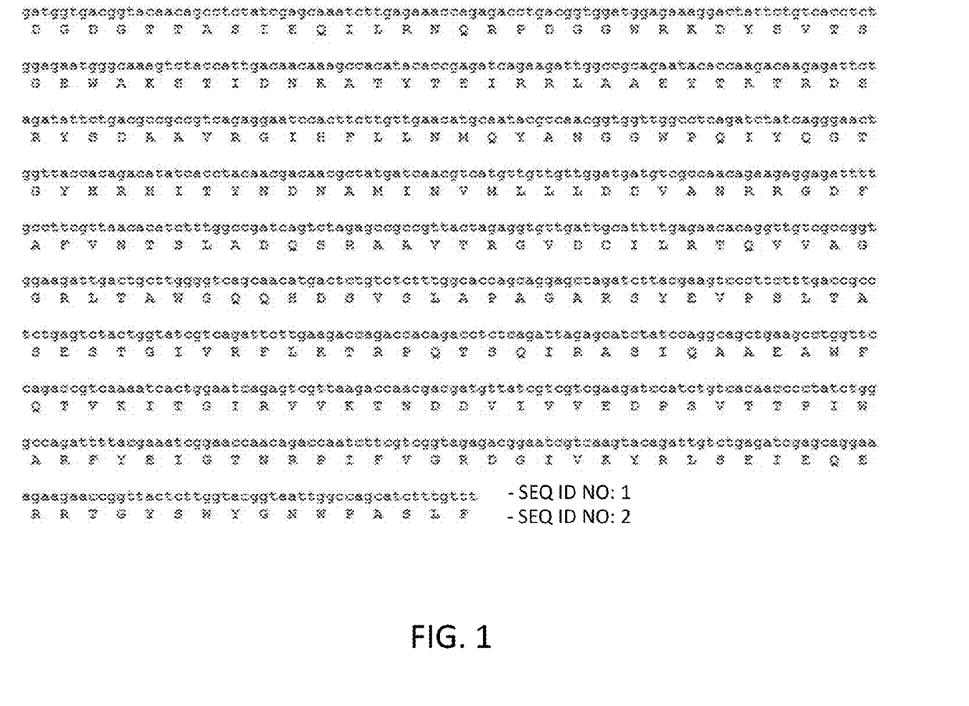
FIG. 1 shows the gene sequence and the amino acid sequence of the wild-type PcPEL.

First, the PcPEL gene was cloned into pPICZαA vector, and as shown in FIG. 1, the PcPEL gene includes 858 base pairs (without stop codon, SEQ ID NO: 1), which encodes a protein of 286 amino acids (SEQ ID NO: 2). The plasmid DNA was linearized and then transformed into *Pichia pastoris*. The transformants were selected on YPD plate with 0.1 mg/ml zeocin and cultured at 30° C. for 2 days. The selected colonies that were individually inoculated in YPD medium were cultured at 30° C. and then were transferred to BMMY containing 0.5% methanol to induce the protein expression. The supernatant that containing induced protein was collected by centrifugation and subsequently dialyzed at least twice against the buffer containing 25 mM Tris, pH 7.5 for following purification. The PcPEL protein was purified by FPLC system using DEAE column. Finally, the purified protein was concentrated to 10 mg/ml for following experiment.

For solving the protein structure of PcPEL by X-ray crystallography, the protein crystal was screened by crystal screen kits using sitting drop vapor diffusion method and then obtained by a condition of 0.1 M Bis-Tris, pH 6.5; 0.2 M Lithium sulfate and 25% PEG3350 at room temperature for 2 days. The phase problem was solved by using molecular replacement method, and the protein structure of PcPEL was subsequently determined by computing.

Figure 2:
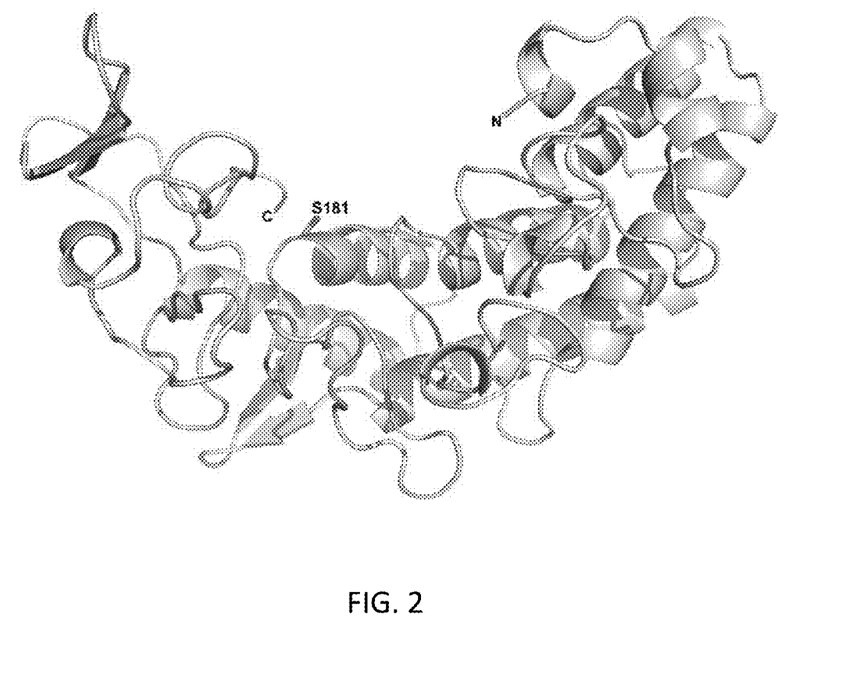
FIG. 2 shows the protein structure of the wild-type PcPEL.

As shown in FIG. 2, the protein structure of PcPEL exhibited the $(\alpha/\alpha)_3$ barrel which is the typical type of PL10 family. The cleft of the protein structure is the active site which allows substrate binding. The present invention tried to improve the thermostability of PcPEL via the increase of hydrophobic interaction. Ser181 which is located near the active site of PcPEL was chosen to be mutated to phenylalanine, methionine and leucine, respectively. The mutants of PcPEL including S181F, S181M and S181L were acquired by using site-directed mutagenesis.

Figure 3:
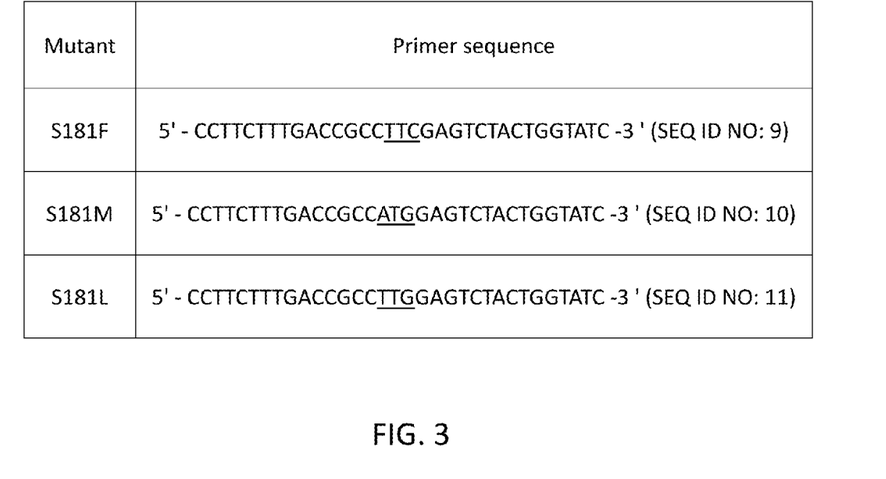
FIG. 3 shows the sequences of the mutagenic primers for the S181F, S181M and S181L mutants.

The mutated genes were separately obtained by PCR method using the designed mutagenic primers shown in FIG. 3, wherein the primer sequences of the three mutants S181F, S181M and S181L were numbered as SEQ ID NO: 9, SEQ ID NO: 10 and SEQ ID NO: 11, respectively. The original template DNA was removed by DpnI. The mutated genes were then individually transformed into E. coli and confirmed the mutation by DNA sequencing. Finally, the mutated genes were separately transformed into P. pastoris and expressed the mutated proteins as previously mentioned.

Figure 4:
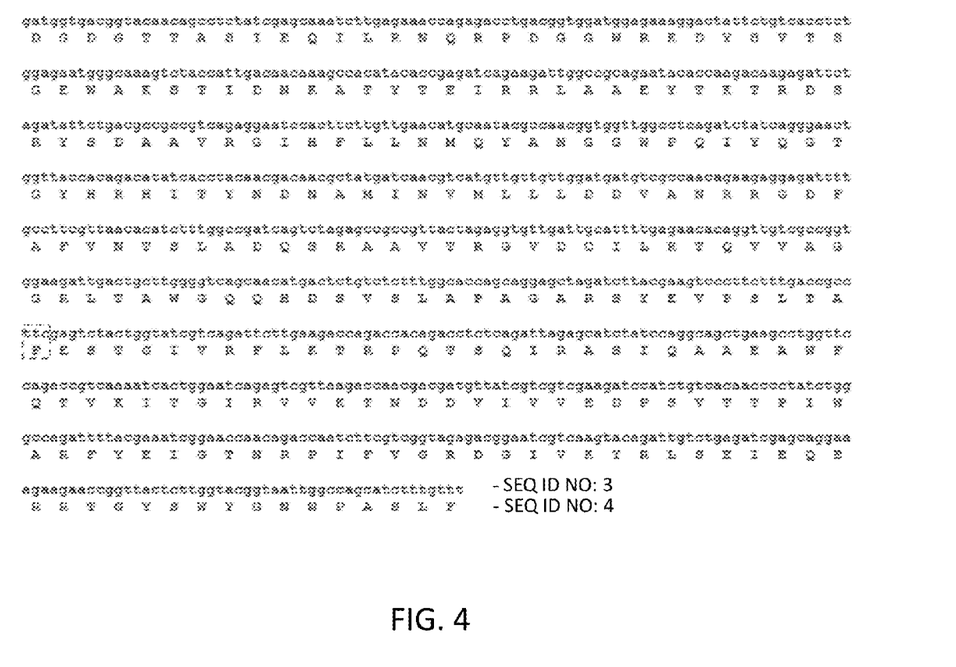
FIG. 4 shows the gene sequence and the amino acid sequence of the S181F mutant.
Figure 5:
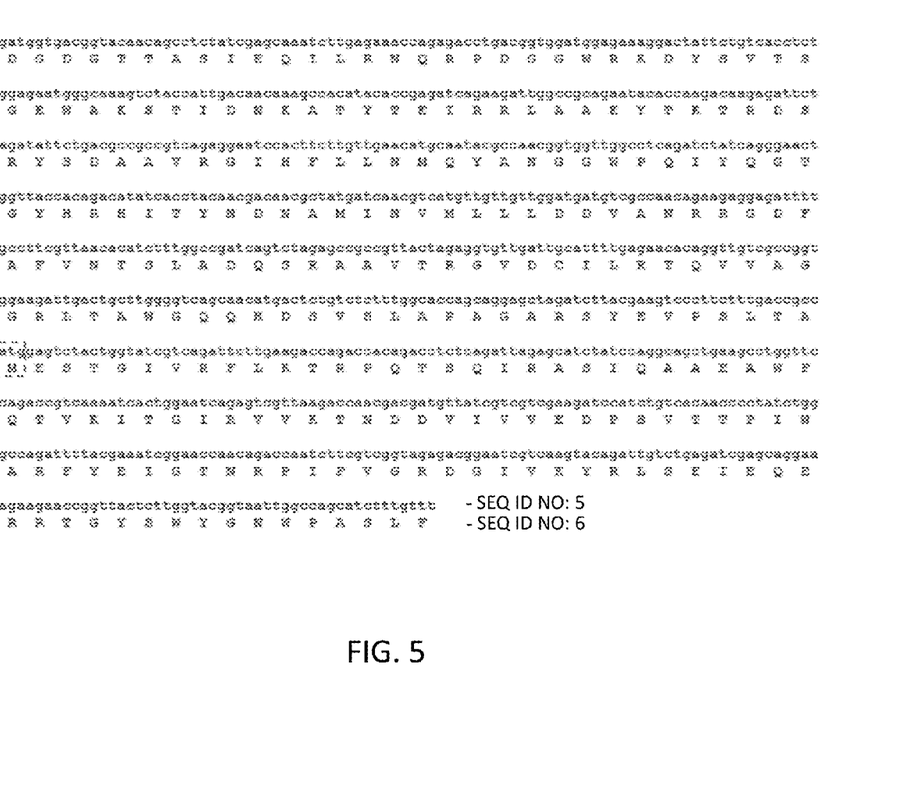
FIG. 5 shows the gene sequence and the amino acid sequence of the S181M mutant.
Figure 6:
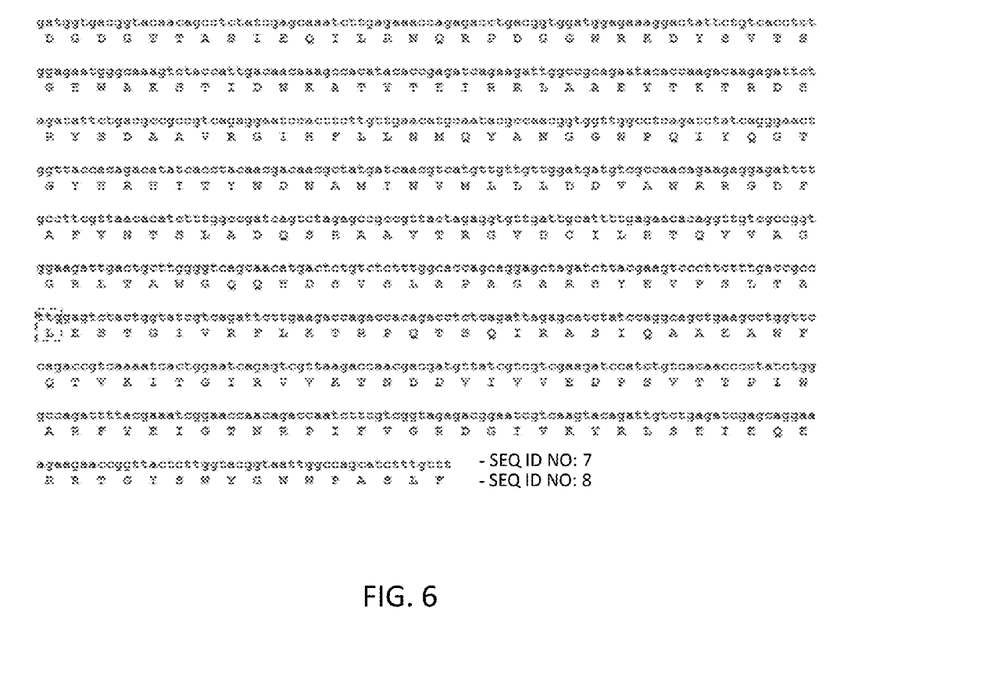
FIG. 6 shows the gene sequence and the amino acid sequence of the S181L mutant.

The gene sequences and the amino acid sequences of the three mutants are shown in FIGS. 4-6, respectively. FIG. 4 shows the gene sequence and the amino acid sequence of the S181F mutant, wherein the gene sequence was numbered as SEQ ID NO: 3, and the amino acid sequence was numbered as SEQ ID NO: 4. FIG. 5 shows the gene sequence and the amino acid sequence of the S181M mutant, wherein the gene sequence was numbered as SEQ ID NO: 5, and the amino acid sequence was numbered as SEQ ID NO: 6. FIG. 6 shows the gene sequence and the amino acid sequence of the S181L mutant, wherein the gene sequence was numbered as SEQ ID NO: 7, and the amino acid sequence was numbered as SEQ ID NO: 8.

The pectate lyase activity was determined by measurement of the increase in the absorbance of unsaturated bonds produced from the cleavage of the polygalacturonic acid (PGA) substrate between C4 and C5 at OD235 nm. The reaction mixture that includes 0.5 ml diluted protein sample and 2 ml 0.2% PGA in pH 9.4 glycine-NaOH buffer containing 0.6 mM $CaCl_2$ was incubated at 45° C. for 10 min. The reaction was then stopped by adding 3 ml 30 mM phosphoric acid. Finally, the absorption of OD235 nm was detected to determine the activity of the pectate lyase.

For the thermostability analysis, all mutants and the wild-type protein were separately incubated at 65° C., 68° C., 70° C. and 75° C. for 2 min and subsequently cooled on ice for 5 min and recovered at room temperature for another 5 min. Finally, the residual enzyme activities of the treated samples were determined as previously mentioned.

Figure 7:
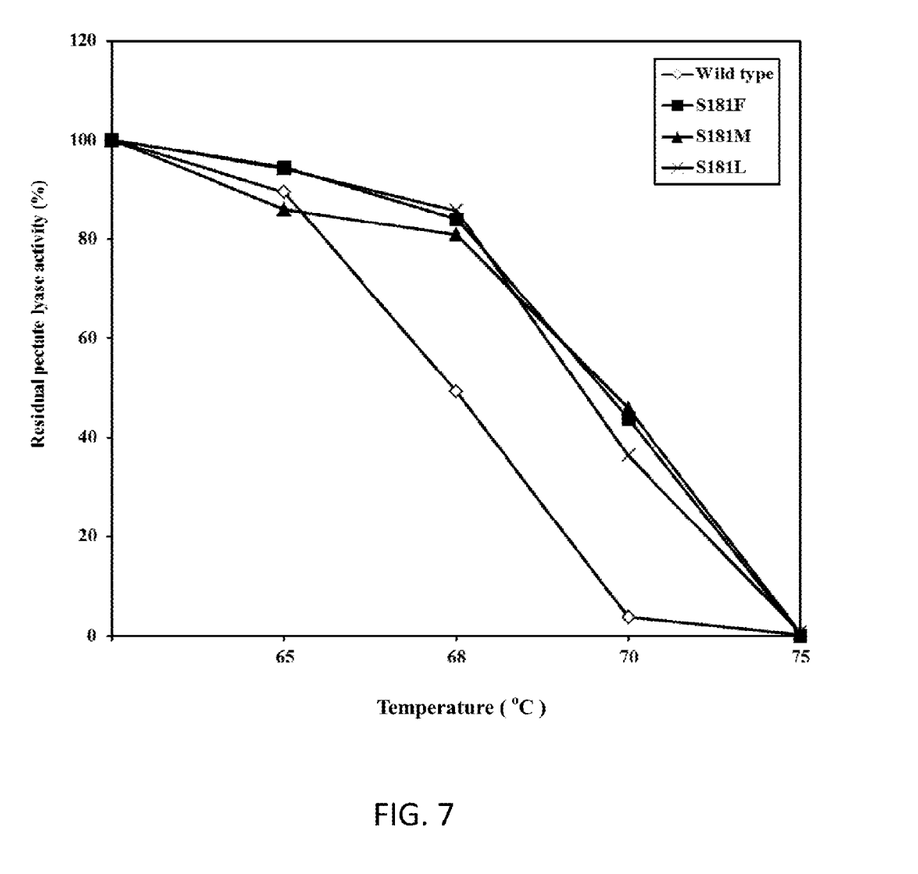
FIG. 7 shows the thermostability analysis of the wild-type PcPEL enzyme and the three mutants S181F, S181M and S181L.

FIG. 7 shows the thermostability analysis of the wild-type PcPEL enzyme and the three mutants S181F, S181M and S181L. The pectate lyase activity of the untreated sample was set to 100%. As shown in FIG. 7, the thermostabilities of S181F, S181M and S181L mutants were all higher than that of the wild type. The residual activity of the wild type after 68° C. heat treatment showed nearly 50% of the untreated original sample. On the other hand, the three mutants all retained 80% activities after the same heat treatment of 68° C. Besides, the wild type almost lost all of its activity after incubation at 70° C. while the three mutants retained about 40% activities. That means the three mutants including S181F, S181M and S181L have higher thermostabilities than the wild type, and thus the three mutants have higher potential for industrial application.

From the above, in order to increase the industrial value of the pectate lyase, the present invention modified PcPEL by rational design to improve the thermostability of PcPEL. According to the structural analysis, Ser181 which is located near the active site of PcPEL was chosen to be mutated to phenylalanine, methionine and leucine, respectively, by site-directed mutagenesis to acquire the three mutants of PcPEL including S181F, S181M and S181L. From the thermostability analysis, the thermostabilities of S181F, S181M and S181L mutants were all higher than that of the wild type. Therefore, the present invention successfully improves the thermostability of PcPEL and further enhances the economic value of this pectate lyase for industrial application.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A pectinase comprising a modified amino acid sequence of SEQ ID NO: 2, wherein the modification is a substitution of serine at position 181 with phenylalanine, methionine or leucine.

2. The pectinase according to claim 1 wherein the amino acid sequence of SEQ ID NO: 2 is encoded by PcPEL gene isolated from *Paenibacillus campinasensis* BL-11.

3. The pectinase according to claim 1 being a pectate lyase.

4. The pectinase according to claim 1 having a full length amino acid sequence of SEQ ID NO: 4.

5. The pectinase according to claim 1 having a full length amino acid sequence of SEQ ID NO: 6.

6. The pectinase according to claim 1 having a full length amino acid sequence of SEQ ID NO: 8.

* * * * *

SEQUENCE LISTING

<160> NUMBER OF SEQ ID NOS: 11

<210> SEQ ID NO 1
<211> LENGTH: 858
<212> TYPE: DNA
<213> ORGANISM: Paenibacillus campinasensis BL-11

<400> SEQUENCE: 1

```
gatggtgacg gtacaacagc ctctatcgag caaatcttga gaaaccagag acctgacggt      60
ggatggagaa aggactattc tgtcacctct ggagaatggg caaagtctac cattgacaac     120
aaagccacat acaccgagat cagaagattg gccgcagaat acaccaagac aagagattct     180
```

```
agatattctg acgccgccgt cagaggaatc cacttcttgt tgaacatgca atacgccaac    240
ggtggttggc ctcagatcta tcagggaact ggttaccaca gacatatcac ctacaacgac    300
aacgctatga tcaacgtcat gttgttgttg gatgatgtcg ccaacagaag aggagatttt    360
gccttcgtta acacatcttt ggccgatcag tctagagccg ccgttactag aggtgttgat    420
tgcattttga gaacacaggt tgtcgccggt ggaagattga ctgcttgggg tcagcaacat    480
gactctgtct ctttggcacc agcaggagct agatcttacg aagtcccttc tttgaccgcc    540
tctgagtcta ctggtatcgt cagattcttg aagaccagac cacagaccct ccagattaga    600
gcatctatcc aggcagctga agcctggttc cagaccgtca aaatcactgg aatcagagtc    660
gttaagacca acgacgatgt tatcgtcgtc gaagatccat ctgtcacaac ccctatctgg    720
gccagatttt acgaaatcgg aaccaacaga ccaatcttcg tcggtagaga cggaatcgtc    780
aagtacagat tgtctgagat cgagcaggaa agaagaaccg ttactcttg gtacggtaat    840
tggccagcat ctttgttt                                                  858

<210> SEQ ID NO 2
<211> LENGTH: 286
<212> TYPE: PRT
<213> ORGANISM: Paenibacillus campinasensis BL-11

<400> SEQUENCE: 2

Asp Gly Asp Gly Thr Thr Ala Ser Ile Glu Gln Ile Leu Arg Asn Gln
1               5                   10                  15

Arg Pro Asp Gly Gly Trp Arg Lys Asp Tyr Ser Val Thr Ser Gly Glu
            20                  25                  30

Trp Ala Lys Ser Thr Ile Asp Asn Lys Ala Thr Tyr Thr Glu Ile Arg
        35                  40                  45

Arg Leu Ala Ala Glu Tyr Thr Lys Thr Arg Asp Ser Arg Tyr Ser Asp
    50                  55                  60

Ala Ala Val Arg Gly Ile His Phe Leu Leu Asn Met Gln Tyr Ala Asn
65                  70                  75                  80

Gly Gly Trp Pro Gln Ile Tyr Gln Gly Thr Gly Tyr His Arg His Ile
                85                  90                  95

Thr Tyr Asn Asp Asn Ala Met Ile Asn Val Met Leu Leu Leu Asp Asp
            100                 105                 110

Val Ala Asn Arg Arg Gly Asp Phe Ala Phe Val Asn Thr Ser Leu Ala
        115                 120                 125

Asp Gln Ser Arg Ala Ala Val Thr Arg Gly Val Asp Cys Ile Leu Arg
    130                 135                 140

Thr Gln Val Val Ala Gly Gly Arg Leu Thr Ala Trp Gly Gln Gln His
145                 150                 155                 160

Asp Ser Val Ser Leu Ala Pro Ala Gly Ala Arg Ser Tyr Glu Val Pro
                165                 170                 175

Ser Leu Thr Ala Ser Glu Ser Thr Gly Ile Val Arg Phe Leu Lys Thr
            180                 185                 190

Arg Pro Gln Thr Ser Gln Ile Arg Ala Ser Ile Gln Ala Ala Glu Ala
        195                 200                 205

Trp Phe Gln Thr Val Lys Ile Thr Gly Ile Arg Val Val Lys Thr Asn
    210                 215                 220

Asp Asp Val Ile Val Val Glu Asp Pro Ser Val Thr Thr Pro Ile Trp
225                 230                 235                 240

Ala Arg Phe Tyr Glu Ile Gly Thr Asn Arg Pro Ile Phe Val Gly Arg
```

```
                    245                 250                 255
Asp Gly Ile Val Lys Tyr Arg Leu Ser Glu Ile Glu Gln Glu Arg Arg
        260                 265                 270

Thr Gly Tyr Ser Trp Tyr Gly Asn Trp Pro Ala Ser Leu Phe
    275                 280                 285
```

<210> SEQ ID NO 3
<211> LENGTH: 858
<212> TYPE: DNA
<213> ORGANISM: Artificial Sequence
<220> FEATURE:
<223> OTHER INFORMATION: Synthetically generated DNA encoding a modified enzyme

<400> SEQUENCE: 3

```
gatggtgacg gtacaacagc ctctatcgag caaatcttga gaaaccagag acctgacggt    60
ggatggagaa aggactattc tgtcacctct ggagaatggg caaagtctac cattgacaac   120
aaagccacat acaccgagat cagaagattg ccgcagaat acaccaagac aagagattct   180
agatattctg acgccgccgt cagaggaatc cacttcttgt tgaacatgca atacgccaac   240
ggtggttggc ctcagatcta tcagggaact ggttaccaca acatatcac ctacaacgac   300
aacgctatga tcaacgtcat gttgttgttg atgatgtcg ccaacagaag aggagatttt   360
gccttcgtta acacatcttt ggccgatcag tctagagccg ccgttactag aggtgttgat   420
tgcattttga aacacaggt tgtcgccggt ggaagattga ctgcttgggg tcagcaacat   480
gactctgtct ctttggcacc agcaggagct agatcttacg aagtcccttc tttgaccgcc   540
ttcgagtcta ctggtatcgt cagattcttg aagaccagac acagacctc tcagattaga   600
gcatctatcc aggcagctga agcctggttc agaccgtca aaatcactgg aatcagagtc   660
gttaagacca cgacgatgt tatcgtcgtc gaagatccat ctgtcacaac ccctatctgg   720
gccagatttt acgaaatcgg aaccaacaga ccaatcttcg tcggtagaga cggaatcgtc   780
aagtacagat tgtctgagat cgagcaggaa agaagaaccg ttactcttg gtacggtaat   840
tggccagcat ctttgttt                                                 858
```

<210> SEQ ID NO 4
<211> LENGTH: 286
<212> TYPE: PRT
<213> ORGANISM: Artificial Sequence
<220> FEATURE:
<223> OTHER INFORMATION: Sequence synthetically translated from SEQ ID
      NO: 3

<400> SEQUENCE: 4

```
Asp Gly Asp Gly Thr Thr Ala Ser Ile Glu Gln Ile Leu Arg Asn Gln
1               5                   10                  15

Arg Pro Asp Gly Gly Trp Arg Lys Asp Tyr Ser Val Thr Ser Gly Glu
            20                  25                  30

Trp Ala Lys Ser Thr Ile Asp Asn Lys Ala Thr Tyr Thr Glu Ile Arg
        35                  40                  45

Arg Leu Ala Ala Glu Tyr Thr Lys Thr Arg Asp Ser Arg Tyr Ser Asp
    50                  55                  60

Ala Ala Val Arg Gly Ile His Phe Leu Leu Asn Met Gln Tyr Ala Asn
65                  70                  75                  80

Gly Gly Trp Pro Gln Ile Tyr Gln Gly Thr Gly Tyr His Arg His Ile
                85                  90                  95

Thr Tyr Asn Asp Asn Ala Met Ile Asn Val Met Leu Leu Leu Asp Asp
```

```
                 100                 105                 110
Val Ala Asn Arg Arg Gly Asp Phe Ala Phe Val Asn Thr Ser Leu Ala
            115                 120                 125

Asp Gln Ser Arg Ala Ala Val Thr Arg Gly Val Asp Cys Ile Leu Arg
    130                 135                 140

Thr Gln Val Val Ala Gly Gly Arg Leu Thr Ala Trp Gly Gln Gln His
145                 150                 155                 160

Asp Ser Val Ser Leu Ala Pro Ala Gly Ala Arg Ser Tyr Glu Val Pro
                165                 170                 175

Ser Leu Thr Ala Phe Glu Ser Thr Gly Ile Val Arg Phe Leu Lys Thr
            180                 185                 190

Arg Pro Gln Thr Ser Gln Ile Arg Ala Ser Ile Gln Ala Ala Glu Ala
        195                 200                 205

Trp Phe Gln Thr Val Lys Ile Thr Gly Ile Arg Val Val Lys Thr Asn
    210                 215                 220

Asp Asp Val Ile Val Glu Asp Pro Ser Val Thr Thr Pro Ile Trp
225                 230                 235                 240

Ala Arg Phe Tyr Glu Ile Gly Thr Asn Arg Pro Ile Phe Val Gly Arg
                245                 250                 255

Asp Gly Ile Val Lys Tyr Arg Leu Ser Glu Ile Glu Gln Glu Arg Arg
            260                 265                 270

Thr Gly Tyr Ser Trp Tyr Gly Asn Trp Pro Ala Ser Leu Phe
        275                 280                 285

<210> SEQ ID NO 5
<211> LENGTH: 858
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
gatggtgacg gtacaacagc ctctatcgag caaatcttga gaaaccagag acctgacggt    60
ggatggagaa aggactattc tgtcacctct ggagaatggg caaagtctac cattgacaac   120
aaagccacat acaccgagat cagaagattg gccgcagaat acaccaagac aagagattct   180
agatattctg acgccgccgt cagaggaatc cacttcttgt tgaacatgca atacgccaac   240
ggtggttggc ctcagatcta tcagggaact ggttaccaca gacatatcac ctacaacgac   300
aacgctatga tcaacgtcat gttgttgttg gatgatgtcg ccaacagaag aggagatttt   360
gccttcgtta acacatcttt ggccgatcag tctagagccg ccgttactag aggtgttgat   420
tgcattttga gaacacaggt tgtcgccggt ggaagattga ctgcttgggg tcagcaacat   480
gactctgtct ctttggcacc agcaggagct agatcttacg aagtcccttc tttgaccgcc   540
atggagtcta ctggtatcgt cagattcttg aagaccagac cacagacctc tcagattaga   600
gcatctatcc aggcagctga agcctggttc cagaccgtca aaatcactgg aatcagagtc   660
gttaagacca cgacgatgt tatcgtcgtc gaagatccat ctgtcacaac ccctatctgg   720
gccagatttt acgaaatcgg aaccaacaga ccaatcttcg tcggtagaga cggaatcgtc   780
aagtacagat tgtctgagat cgagcaggaa agaagaaccg gttactcttg gtacggtaat   840
tggccagcat ctttgttt                                                858

<210> SEQ ID NO 6
<211> LENGTH: 286
```

```
<212> TYPE: PRT
<213> ORGANISM: Artificial Sequence
<220> FEATURE:
<223> OTHER INFORMATION: Sequence synthetically translated from SEQ ID
      NO: 5

<400> SEQUENCE: 6

Asp Gly Asp Gly Thr Thr Ala Ser Ile Glu Gln Ile Leu Arg Asn Gln
1               5                   10                  15

Arg Pro Asp Gly Gly Trp Arg Lys Asp Tyr Ser Val Thr Ser Gly Glu
            20                  25                  30

Trp Ala Lys Ser Thr Ile Asp Asn Lys Ala Thr Tyr Thr Glu Ile Arg
        35                  40                  45

Arg Leu Ala Ala Glu Tyr Thr Lys Thr Arg Asp Ser Arg Tyr Ser Asp
    50                  55                  60

Ala Ala Val Arg Gly Ile His Phe Leu Leu Asn Met Gln Tyr Ala Asn
65                  70                  75                  80

Gly Gly Trp Pro Gln Ile Tyr Gln Gly Thr Gly Tyr His Arg His Ile
                85                  90                  95

Thr Tyr Asn Asp Asn Ala Met Ile Asn Val Met Leu Leu Leu Asp Asp
            100                 105                 110

Val Ala Asn Arg Arg Gly Asp Phe Ala Phe Val Asn Thr Ser Leu Ala
        115                 120                 125

Asp Gln Ser Arg Ala Ala Val Thr Arg Gly Val Asp Cys Ile Leu Arg
    130                 135                 140

Thr Gln Val Val Ala Gly Gly Arg Leu Thr Ala Trp Gly Gln Gln His
145                 150                 155                 160

Asp Ser Val Ser Leu Ala Pro Ala Gly Ala Arg Ser Tyr Glu Val Pro
                165                 170                 175

Ser Leu Thr Ala Met Glu Ser Thr Gly Ile Val Arg Phe Leu Lys Thr
            180                 185                 190

Arg Pro Gln Thr Ser Gln Ile Arg Ala Ser Ile Gln Ala Ala Glu Ala
        195                 200                 205

Trp Phe Gln Thr Val Lys Ile Thr Gly Ile Arg Val Val Lys Thr Asn
    210                 215                 220

Asp Asp Val Ile Val Val Glu Asp Pro Ser Val Thr Thr Pro Ile Trp
225                 230                 235                 240

Ala Arg Phe Tyr Glu Ile Gly Thr Asn Arg Pro Ile Phe Val Gly Arg
                245                 250                 255

Asp Gly Ile Val Lys Tyr Arg Leu Ser Glu Ile Glu Gln Glu Arg Arg
            260                 265                 270

Thr Gly Tyr Ser Trp Tyr Gly Asn Trp Pro Ala Ser Leu Phe
        275                 280                 285

<210> SEQ ID NO 7
<211> LENGTH: 858
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 7
gatggtgacg gtacaacagc ctctatcgag caaatcttga gaaaccagag acctgacggt      60
ggatggagaa aggactattc tgtcacctct ggagaatggg caaagtctac cattgacaac     120
aaagccacat acaccgagat cagaagattg gccgcagaat acaccaagac aagagattct     180
```

```
agatattctg acgccgccgt cagaggaatc cacttcttgt tgaacatgca atacgccaac    240
ggtggttggc ctcagatcta tcagggaact ggttaccaca gacatatcac ctacaacgac    300
aacgctatga tcaacgtcat gttgttgttg gatgatgtcg ccaacagaag aggagatttt    360
gccttcgtta acacatcttt ggccgatcag tctagagccg ccgttactag aggtgttgat    420
tgcattttga gaacacaggt tgtcgccggt ggaagattga ctgcttgggg tcagcaacat    480
gactctgtct ctttggcacc agcaggagct agatcttacg aagtcccttc tttgaccgcc    540
ttggagtcta ctggtatcgt cagattcttg aagaccagac cacagacctc tcagattaga    600
gcatctatcc aggcagctga agcctggttc cagaccgtca aaatcactgg aatcagagtc    660
gttaagacca acgacgatgt tatcgtcgtc gaagatccat ctgtcacaac ccctatctgg    720
gccagatttt acgaaatcgg aaccaacaga ccaatcttcg tcggtagaga cggaatcgtc    780
aagtacagat tgtctgagat cgagcaggaa agaagaaccg ttactcttg gtacggtaat    840
tggccagcat ctttgttt                                                   858
```

<210> SEQ ID NO 8
<211> LENGTH: 286
<212> TYPE: PRT
<213> ORGANISM: Artificial Sequence
<220> FEATURE:
<223> OTHER INFORMATION: Sequence synthetically translated from SEQ ID
      NO: 7

<400> SEQUENCE: 8

```
Asp Gly Asp Gly Thr Thr Ala Ser Ile Glu Gln Ile Leu Arg Asn Gln
1               5                   10                  15

Arg Pro Asp Gly Gly Trp Arg Lys Asp Tyr Ser Val Thr Ser Gly Glu
            20                  25                  30

Trp Ala Lys Ser Thr Ile Asp Asn Lys Ala Thr Tyr Thr Glu Ile Arg
        35                  40                  45

Arg Leu Ala Ala Glu Tyr Thr Lys Thr Arg Asp Ser Arg Tyr Ser Asp
    50                  55                  60

Ala Ala Val Arg Gly Ile His Phe Leu Leu Asn Met Gln Tyr Ala Asn
65                  70                  75                  80

Gly Gly Trp Pro Gln Ile Tyr Gln Gly Thr Gly Tyr His Arg His Ile
                85                  90                  95

Thr Tyr Asn Asp Asn Ala Met Ile Asn Val Met Leu Leu Asp Asp
            100                 105                 110

Val Ala Asn Arg Arg Gly Asp Phe Ala Phe Val Asn Thr Ser Leu Ala
        115                 120                 125

Asp Gln Ser Arg Ala Ala Val Thr Arg Gly Val Asp Cys Ile Leu Arg
    130                 135                 140

Thr Gln Val Val Ala Gly Gly Arg Leu Thr Ala Trp Gly Gln Gln His
145                 150                 155                 160

Asp Ser Val Ser Leu Ala Pro Ala Gly Ala Arg Ser Tyr Glu Val Pro
                165                 170                 175

Ser Leu Thr Ala Leu Glu Ser Thr Gly Ile Val Arg Phe Leu Lys Thr
            180                 185                 190

Arg Pro Gln Thr Ser Gln Ile Arg Ala Ser Ile Gln Ala Ala Glu Ala
        195                 200                 205

Trp Phe Gln Thr Val Lys Ile Thr Gly Ile Arg Val Val Lys Thr Asn
    210                 215                 220

Asp Asp Val Ile Val Val Glu Asp Pro Ser Val Thr Thr Pro Ile Trp
225                 230                 235                 240
```

Ala Arg Phe Tyr Glu Ile Gly Thr Asn Arg Pro Ile Phe Val Gly Arg
            245                 250                 255

Asp Gly Ile Val Lys Tyr Arg Leu Ser Glu Ile Glu Gln Glu Arg Arg
            260                 265                 270

Thr Gly Tyr Ser Trp Tyr Gly Asn Trp Pro Ala Ser Leu Phe
            275                 280                 285

<210> SEQ ID NO 9
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 9
ccttctttga ccgccttcga gtctactggt atc                                    33

<210> SEQ ID NO 10
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 10
ccttctttga ccgccatgga gtctactggt atc                                    33

<210> SEQ ID NO 11
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 11
ccttctttga ccgccttgga gtctactggt atc                                    33